United States Patent [19]

Kopecky

[11] Patent Number: 5,627,870

[45] Date of Patent: May 6, 1997

[54] DEVICE FOR TREATING CEREBRAL LESIONS BY GAMMA RADIATION, AND CORRESPONDING TREATMENT APPARATUS

[75] Inventor: Bernard Kopecky, Nantes, France

[73] Assignee: ATEA, Societe Atlantique De Techniques Avancees, Carquefou, France

[21] Appl. No.: 381,858

[22] PCT Filed: Jun. 6, 1994

[86] PCT No.: PCT/FR94/00667

§ 371 Date: Apr. 14, 1995

§ 102(e) Date: Apr. 14, 1995

[87] PCT Pub. No.: WO94/28973

PCT Pub. Date: Dec. 22, 1994

[30] Foreign Application Priority Data

Jun. 7, 1993 [FR] France .................................. 93 06787

[51] Int. Cl.[6] .................................................. A61N 5/10
[52] U.S. Cl. .................................................. 378/65; 378/68
[58] Field of Search .................................. 378/64, 65, 68

[56] References Cited

U.S. PATENT DOCUMENTS

| 4,780,898 | 10/1988 | Sundqvist | 378/65 |
| 5,528,653 | 6/1996 | Song et al. | 378/65 |

FOREIGN PATENT DOCUMENTS

| 248774 | 12/1987 | European Pat. Off. . |
| 371303 | 6/1990 | European Pat. Off. . |
| 431785 | 6/1991 | European Pat. Off. . |
| 2672220 | 8/1992 | France . |

OTHER PUBLICATIONS

Search Report FR 93 06787 1994.

*Primary Examiner*—David P. Porta
*Assistant Examiner*—David Vernon Bruce
*Attorney, Agent, or Firm*—Pollock, Vande Sande & Priddy

[57] ABSTRACT

A device for treating cerebral lesions by gamma radiation, comprising an approximately semi-spherical source-collimator assembly having a large number of gamma ray sources associated with channels directed to the same focal point. Each gamma ray source is associated with a group of channels arranged in the manner of a cone, the apex of which is at the focal point.

6 Claims, 3 Drawing Sheets

DEVICE FOR TREATING CEREBRAL LESIONS BY GAMMA RADIATION, AND CORRESPONDING TREATMENT APPARATUS

FIELD OF THE INVENTION

The present invention relates to a device for treating cerebral lesions by gamma radiation, of the type comprising an approximately hemispherical source/collimator assembly which includes a large number of gamma-ray sources associated with channels which are all oriented towards one and the same focusing point.

BACKGROUND OF THE INVENTION

Gamma-radiation apparatuses have been proposed for non-invasive neurosurgery of the brain in order to treat cerebral lesions without opening the cranium. Destruction of the lesions is achieved by precisely concentrating gamma radiation onto the areas to be treated, such as venous malformations or tumors. These apparatuses are often designated by the name "gamma surgical apparatuses" or "gamma bistouries".

In these apparatuses, external gamma-radiation sources are used, the radiation being directed and concentrated, in a precise manner, onto the treated lesion in order for the desired dose to be absorbed by this lesion without appreciably damaging the intermediate tissues intervening between the sources and the lesion, nor the tissues surrounding the lesion and, in a general manner, reducing to a minimum the radiation doses absorbed by the healthy tissues.

This is achieved especially by the devices of the aforementioned type, an example of which is described in FR-A-2,672,220. In this technology, a large number of fixed external sources are used, these being collimated individually and arranged radially so that the axes of the rays that they produce converge onto a focal point which coincides with the lesion to be treated. The intensity of each beam is insufficient to damage the intermediate healthy tissues through which it passes, especially as the device is given, during the treatment, an angular movement about the focusing point. In contrast, at the point of convergence or focal point, the dose received by the lesion is sufficient to destroy it.

In this known technique, each source is associated with an at least approximately conical single channel, the generatrices of which converge towards the focusing point and in which a conical central needle made of a material absorbing the gamma rays is positioned.

SUMMARY OF THE INVENTION

The object of the invention is to improve this known device so as better to concentrate the radiation at the focusing point in order to improve the effectiveness of the treatment, while at the same time better protecting the healthy areas in the brain from the gamma radiation.

For this purpose, the invention is a treatment device of the aforementioned type, in which each gamma-ray source is associated with a bundle of channels bounded by a conical envelope of revolution, the vertex of which is located at the focusing point.

The device may include one or more of the following characteristics:

each source lies opposite the entrance opening of all the channels of the bundle which is associated with it;

all the channels are cylindrical;

all the channels have substantially the same dimensions;

each bundle includes at least five channels.

The invention also relates to an apparatus for treating cerebral lesions by gamma radiation, comprising a device such as defined hereinabove, and a movable patient-supporting table equipped with a stereotactic device intended to interact with the patient's head.

BRIEF DESCRIPTION OF THE DRAWINGS

An illustrative embodiment of the invention will now be described with reference to the appended drawings, in which.

DETAILED DESCRIPTION

Figure 1:
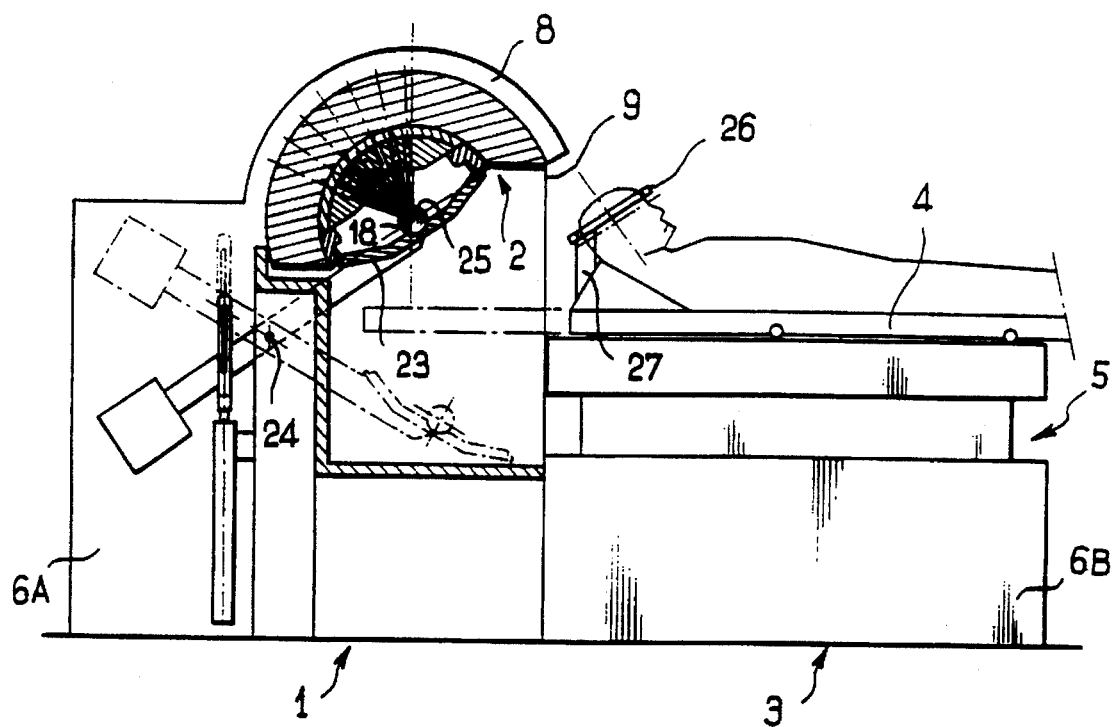
FIG. 1 is a schematic overall view, in side elevation and partly in section, of a treatment apparatus in accordance with the invention, in the stand-by position.
Figure 2:
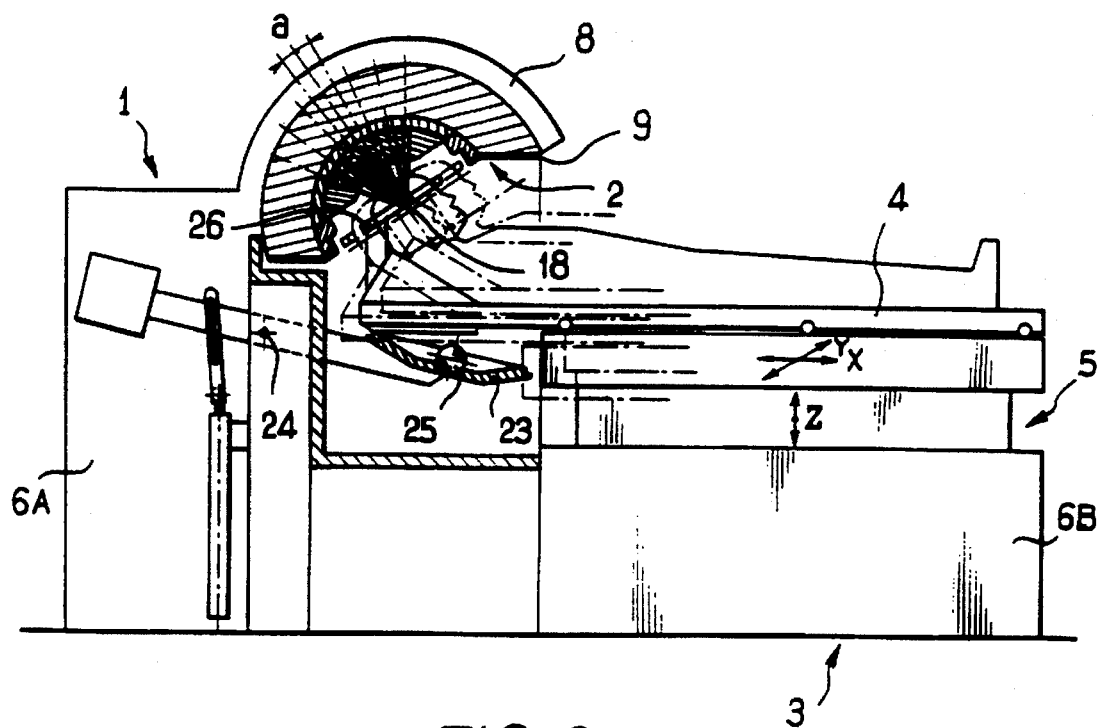
FIG. 2 depicts, in a similar manner, the apparatus during treatment.

The apparatus for treating cerebral lesions, depicted in FIGS. 1 and 2, is of the type described in the aforementioned FR-A-2,672,220. It comprises a fixed main frame 1 in the upper part of which a source/collimator assembly 2 is mounted. Attached to this frame is a fixed secondary frame 3 which supports a patient-supporting table 4, this being achieved by means of a numerical-control motorized device 5 which enables the table to be moved parallel to itself in three orthogonal directions, X (which is the longitudinal direction of the table), Y and Z (vertical direction). The frames 1 and 3 contain, moreover, appropriate electronic calculating means for the control, these being shown schematically at 6A and 6B, respectively, in order to provide the operation which will be described hereinbelow.

Figure 3:
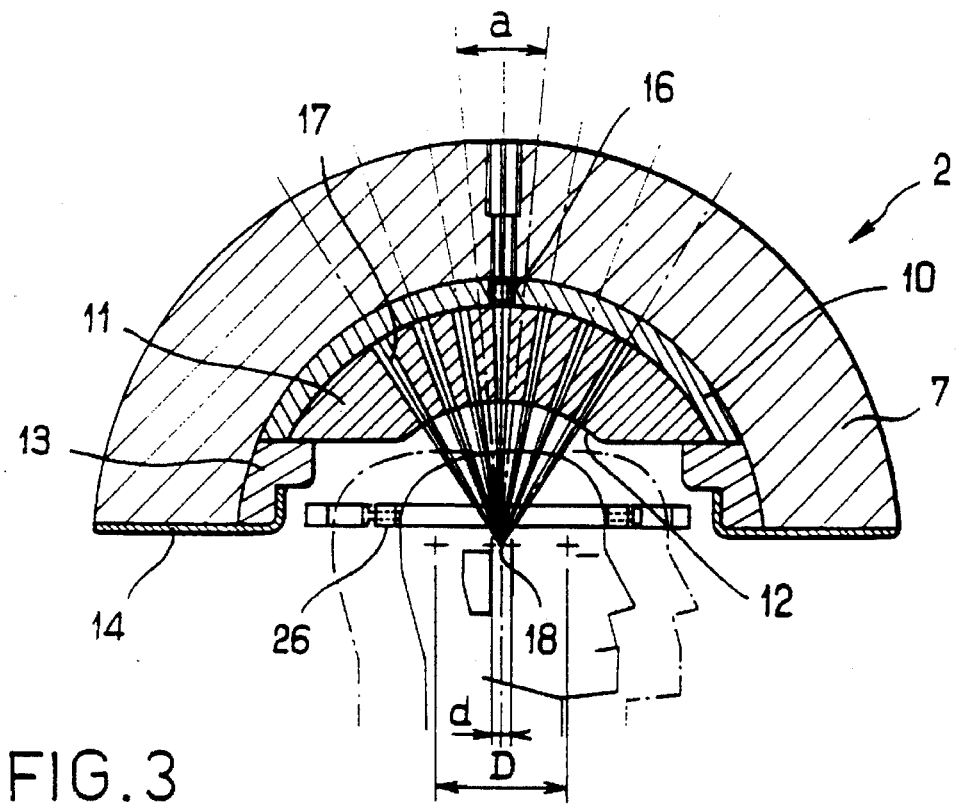
FIG. 3 is a side-on view of the source/collimator assembly indicating the possible positions of the patient's head.
Figure 4:
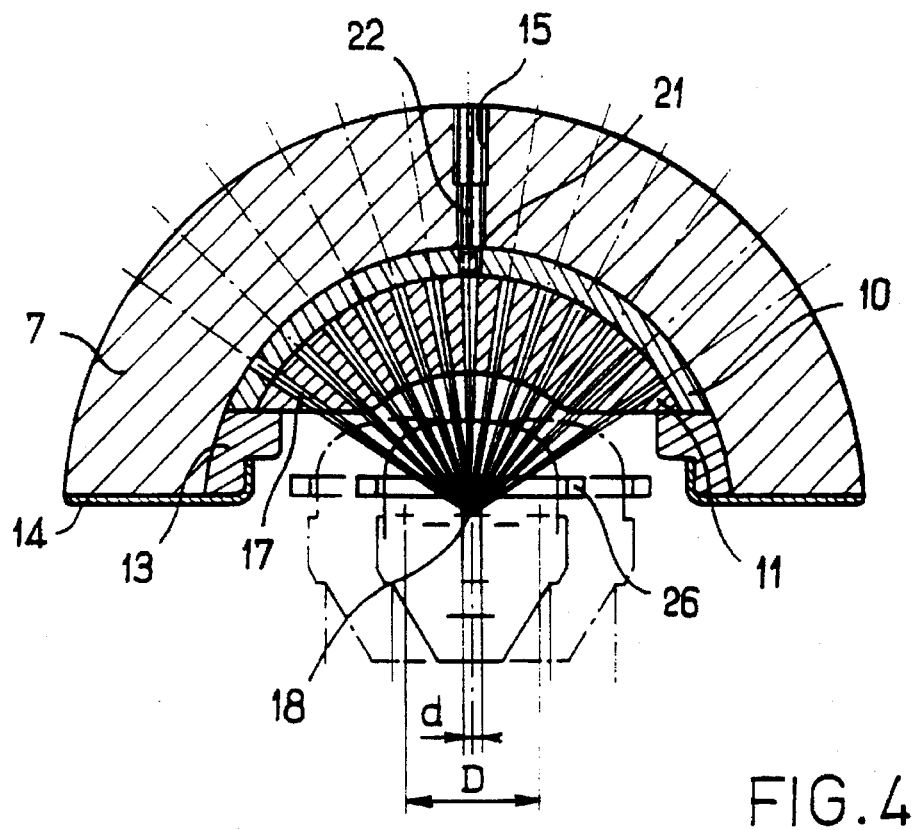
FIG. 4 is a front view of the subject of FIG. 3.

The source/collimator assembly 2, which may be seen better in FIGS. 3 and 4, has a substantially hemispherical general shape. It comprises a thick external shield 7, made of pure or low-alloy lead, the external surface of which matches, with a small radial clearance, the internal surface of a shell 8 of the frame 1. This shell is closed on all sides, with the exception of a front opening 9 just sufficient to allow passage of the table 4 supporting a patient.

Positioned in the shield 7 are, a thin source-holder 10 and, on the inside of the latter, a thick collimator 11 defining a spherical internal surface 12. The members 10 and 11 are fixed in the shield by means of a peripheral ring 13 which is itself held by a crimped annular flange 14.

Passing right through the central region of assembly 2, shown in the side-on view (FIG. 3) and over a greater angular extent in the front view (FIG. 4), is a large number of groups of radial channels. Each group consists of a stepped outer channel 15 passing through the shield, of a cylindrical channel 16 passing through the source holder and of a bundle of channels 17 passing through the collimator. The axes of all these channels converge towards a focusing point 18, which is the center of the sphere.

Figure 5:
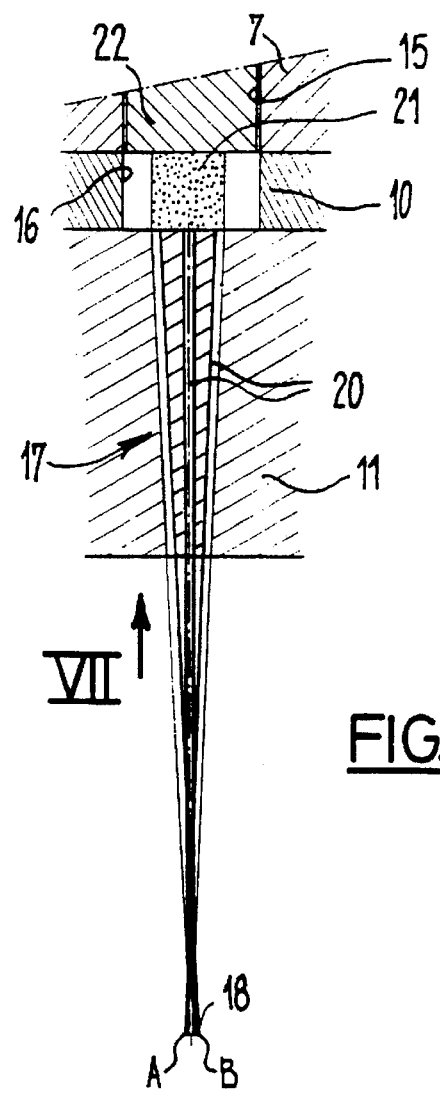
FIG. 5 depicts, in longitudinal section and on a larger scale, the region of the source/collimator assembly associated with a source.
Figure 6:
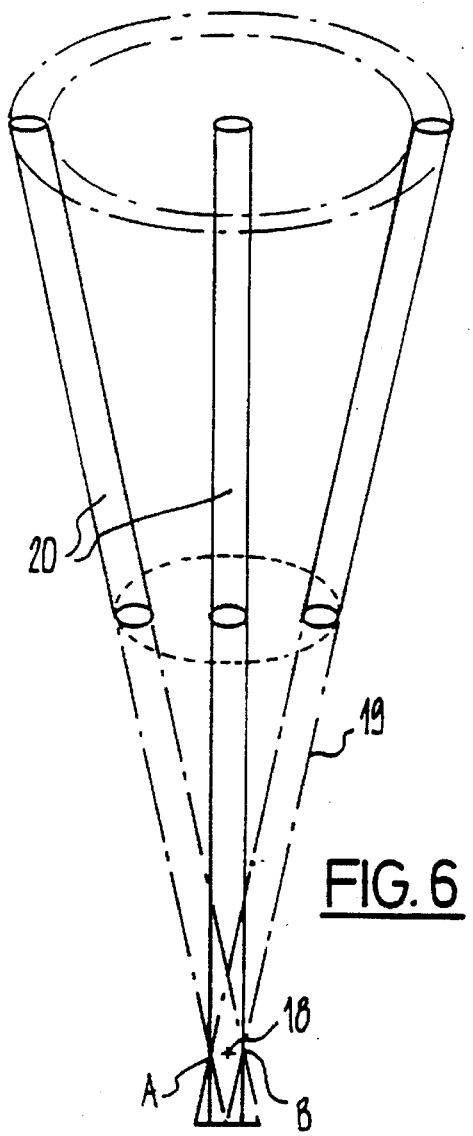
FIG. 6 illustrates, in perspective, the set of channels associated with a source.
Figure 7:
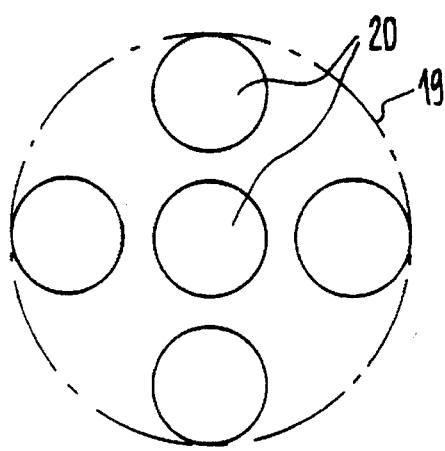
FIG. 7 is a view taken in the direction of FIG. 5.

As depicted in FIGS. 5 to 7, each bundle 17 is bounded by an imaginary cone-shaped envelope 19, the vertex of which is located at the point 18. The large base and the small base of the envelope 19, in the region of the external and internal surfaces of the collimator 11, have, respective, diameters of the order of 20 mm and 10 mm. The bundle 17 consists of a certain number of fine cylindrical channels 20, all the axes of which converge towards the point 18. The diameter of each channel 20 is of the order of 2 to 3 mm and the number of channels in one bundle depends on the space available in the envelope 19. This number is, for example, five or more, as illustrated in FIG. 7.

The bulk of the collimator 11 consists of a highly gamma-ray absorbent material, especially pure or low-alloy lead or natural uranium or uranium depleted of isotope 235, rendered non-oxidizable by disposition of a protective layer or by alloying, especially on the wall of each channel 20.

A caesium 137 gamma-ray source, of cylindrical shape, the diameter of which is approximately equal to the large diameter of the envelope 19, is arranged in the channel 16 and held in place therein by a pressing member 22 inserted into and appropriately fixed in the channel 15 (FIGS. 3 and 4).

A port 23 is mounted so as to tilt on the frame 1 about a horizontal and transverse spindle 24 and carries a block 25 consisting of a highly gamma-ray absorbent material, for example uranium.

The table 4 carries a stereotactic device 26 supported by uprights 27 fixed to the table.

The operation of the apparatus will now be described.

A preliminary investigation phase has allowed the patient's head to be positioned in the stereotactic 26 device and the lesion to be treated to be identified in space.

For the treatment, the table 4 being removed from the frame 1 (FIG. 1), the patient's head is firstly repositioned in the same manner. The port 23 is then closed and is applied to the perimeter of the ring 13, and the block 25 lies at the focusing point 18 and absorbs the focused gamma rays.

Next, the port 23 is opened and the patient's head is inserted under the collimator via the opening 9, the table being made to carry out a first approach movement in directions X and Z and then a final adjustment movement in directions X and Y of the order of ±70 mm (reference D in FIGS. 3 and 4). This brings the lesion, identified by means of the device 26, into coincidence with the point 18. The head then lies at an appreciable radial distance from the internal surface 12 of the assembly 2, which distance is very much greater than the dimensions of the lesion to be treated.

Then, during the treatment, the contour of the lesion is followed by means of small movements of the table in directions X, Y and Z, of the order of ±10 mm, called treatment movements (reference d in FIGS. 3 and 4). Simultaneously, the collimator is given an oscillatory movement, with a small angle a of approximately ±5°, about the aforementioned spindle which passes through the gamma-ray focusing point (FIG. 3).

The three-dimensional movement of the table 4 is very precise, of the type used in certain numerical-control machine tools. It is controlled by a computer, on the basis of medical-imaging data obtained using a scanner, magnetic resonance or other techniques. It enables, from just the one initial adjustment, arbitrarily shaped lesions to be treated very accurately in a single operation.

The oscillatory movement of the assembly 2 enables the healthy tissues, located between it and the focusing point, not to be damaged, and it also enables any contact of particularly sensitive areas in the brain with the gamma rays to be avoided.

Figure 8:
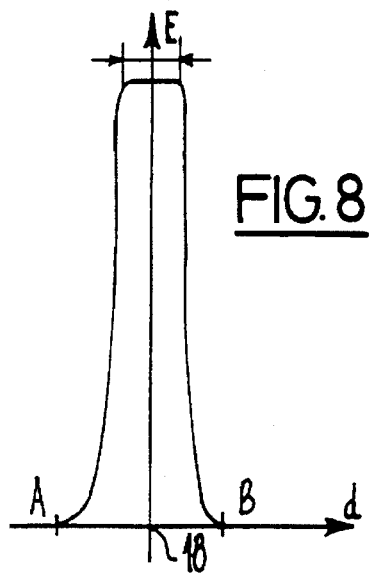
FIG. 8 illustrates, by means of a diagram, the energy-flux distribution in the vicinity of the focusing point.

Moreover, each surface element of the source, located opposite a channel, emits radiation which will either be absorbed by the wall of this channel or will pass to the point 18 or very close to it. In particular, in a plane perpendicular to the central axis of the envelope 20, the entire beam is concentrated onto a very small length AB (FIGS. 5 and 6). In addition, as depicted in FIG. 8, where the cumulative energy E of the gamma rays is plotted as ordinates and the distance d from the point 18 as abscissae, virtually the entire energy of the gamma rays is concentrated in the region which immediately surrounds the focal point 18, forming an almost rectangular pulse, the energy being virtually zero at the points A and B. In other words, a relatively narrow focal spot is obtained, which spot typically has a diameter of the order of a few mm, especially 2 to 4 mm, and in which virtually all the gamma energy is concentrated.

I claim:

1. Device for treating cerebral lesions by gamma radiation, of the type comprising an approximately hemispherical source/collimator assembly (2) which includes a large number of gamma-ray sources (21) associated with channels (20) which are all oriented towards one and the same focusing point (18), characterized in that each gamma-ray source (21) is associated with a bundle (17) of channels (20) bounded by a conical envelope of revolution (19), the vertex of which is located at the focusing point (18).

2. Device according to claim 1, wherein each source (21) lies opposite the entrance opening of all the channels (20) of the bundle (17) which is associated with it.

3. Device according to claim 1 wherein all the channels (20) are cylindrical.

4. Device according to claim 1 wherein all the channels (20) have substantially the same dimensions.

5. Device according to claim 1, wherein each bundle (17) includes at least five channels (20).

6. Apparatus for treating cerebral lesions by gamma radiation, comprising a device according to claim 1, and a movable patient-supporting table (4) equipped with a stereotactic device (26) intended to interact with the patient's head.

* * * * *